United States Patent
Ooten

(10) Patent No.: US 9,352,063 B2
(45) Date of Patent: May 31, 2016

(54) HVAC FRAGRANCE SYSTEM

(71) Applicant: Lashell Ooten, Victorville, CA (US)

(72) Inventor: Lashell Ooten, Victorville, CA (US)

( * ) Notice: Subject to any disclaimer, the term of this patent is extended or adjusted under 35 U.S.C. 154(b) by 37 days.

(21) Appl. No.: 14/248,489

(22) Filed: Apr. 9, 2014

(65) Prior Publication Data

US 2015/0030498 A1    Jan. 29, 2015

Related U.S. Application Data

(60) Provisional application No. 61/809,372, filed on Jul. 23, 2013.

(51) Int. Cl.
*A61L 9/12*      (2006.01)
*A61L 9/04*      (2006.01)
*F24F 3/16*      (2006.01)

(52) U.S. Cl.
CPC . *A61L 9/122* (2013.01); *A61L 9/04* (2013.01); *A61L 9/127* (2013.01); *F24F 3/16* (2013.01); *A61L 2209/16* (2013.01); *F24F 2003/1689* (2013.01)

(58) Field of Classification Search
CPC ........... A61L 9/122; A61L 9/04; A61L 9/127; A61L 2209/16; F24F 3/16; F24F 2003/1689
See application file for complete search history.

(56) References Cited

U.S. PATENT DOCUMENTS

| | | | | |
|---|---|---|---|---|
| 4,102,656 | A * | 7/1978 | Koritz | 96/222 |
| 7,824,051 | B2 * | 11/2010 | Walter et al. | 362/101 |
| 7,854,394 | B2 | 12/2010 | Powell et al. | |
| 8,119,064 | B2 * | 2/2012 | Woo et al. | 422/5 |
| 8,372,349 | B1 * | 2/2013 | Shotey et al. | 422/306 |
| 2002/0090318 | A1 * | 7/2002 | Challand et al. | 422/5 |
| 2002/0114744 | A1 * | 8/2002 | Chiao et al. | 422/124 |
| 2003/0186643 | A1 | 10/2003 | Feuillard et al. | |
| 2003/0223040 | A1 * | 12/2003 | Schermerhorn | G03B 21/32 352/85 |
| 2004/0028551 | A1 * | 2/2004 | Kvietok et al. | 422/4 |
| 2006/0121844 | A1 * | 6/2006 | Sparks | A61L 9/14 454/337 |
| 2006/0154642 | A1 * | 7/2006 | Scannell, Jr. | 455/404.1 |

(Continued)

FOREIGN PATENT DOCUMENTS

| EP | 1439083 | 7/2004 |
|---|---|---|
| EP | 1645295 | 4/2006 |

(Continued)

OTHER PUBLICATIONS

"2014 Mercedes-Benz S-Class: Spa on Wheels, The Smell of Luxury," Forbes, Apr. 1, 2013, retrieved Mar. 24, 2014, http://www.forbes.com/pictures/egdh45turthk/the-smell-of-luxury/, 2 pages.

(Continued)

*Primary Examiner* — Regina M Yoo
(74) *Attorney, Agent, or Firm* — Fish & Richardson P.C.

(57) ABSTRACT

Fragrance systems are provided that can be used in conjunction with heating, ventilation, and air-conditioning systems. The fragrance systems can inject a fragrance into an airstream that is supplied to a space such as a room of a building or a vehicle cabin. In some embodiments, the speed a fan of the fragrance system can be automatically modulated in a predetermined relationship to the speed of a fan of the HVAC system. Accordingly, a desired level of fragrance can be automatically maintained as desired within the airstream that is supplied to the space, even when the HVAC fan speed or other conditions fluctuate.

16 Claims, 5 Drawing Sheets

(56) References Cited

U.S. PATENT DOCUMENTS

| | | |
|---|---|---|
| 2006/0263734 A1* | 11/2006 | Kubicek et al. ............... 431/298 |
| 2007/0181000 A1* | 8/2007 | Wilson et al. ................... 96/134 |
| 2008/0206092 A1* | 8/2008 | Crapser et al. ..................... 422/5 |
| 2010/0003164 A1* | 1/2010 | Bourne et al. ..................... 422/4 |
| 2010/0061896 A1* | 3/2010 | Sassoon ........................ 422/124 |
| 2011/0091354 A1* | 4/2011 | Schwartz et al. ............... 422/28 |
| 2011/0203040 A1* | 8/2011 | Brown .......................... 4/209 R |
| 2012/0024979 A1 | 2/2012 | Wadlin |
| 2013/0134233 A1* | 5/2013 | Woo et al. ....................... 239/13 |
| 2013/0309102 A1* | 11/2013 | Gruenbacher et al. .......... 417/54 |

FOREIGN PATENT DOCUMENTS

| | | |
|---|---|---|
| EP | 2011677 | 1/2009 |
| EP | 2065234 | 6/2009 |

OTHER PUBLICATIONS

Aukofer, "New Mercedes-Benz S-Class offer perfume as optional feature," *Long Island Newsday*, Jul. 16, 2013, retrieved Mar. 24, 2014, http://www.newsday.com/classifieds/cars/new-mercedes-benz-s-class-offers-perfume-as-optional-feature-1.5703321, 4 pages.

* cited by examiner

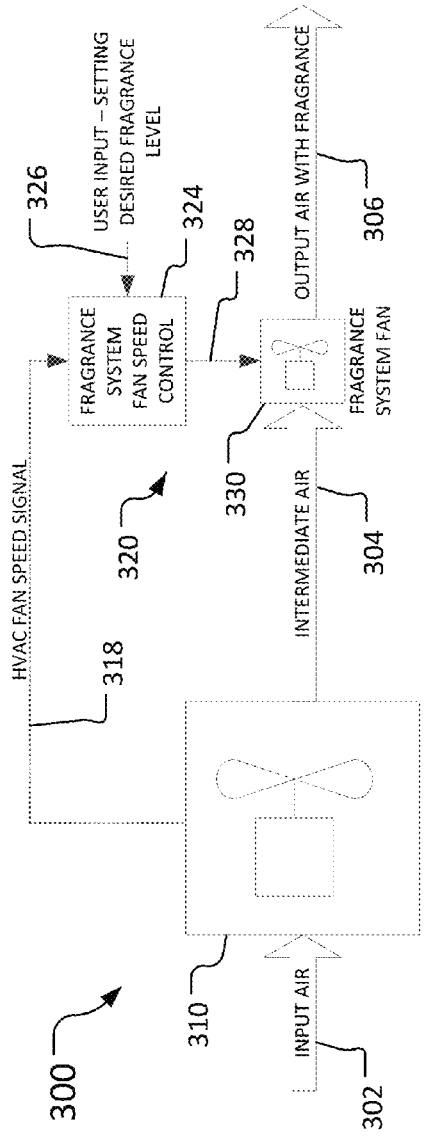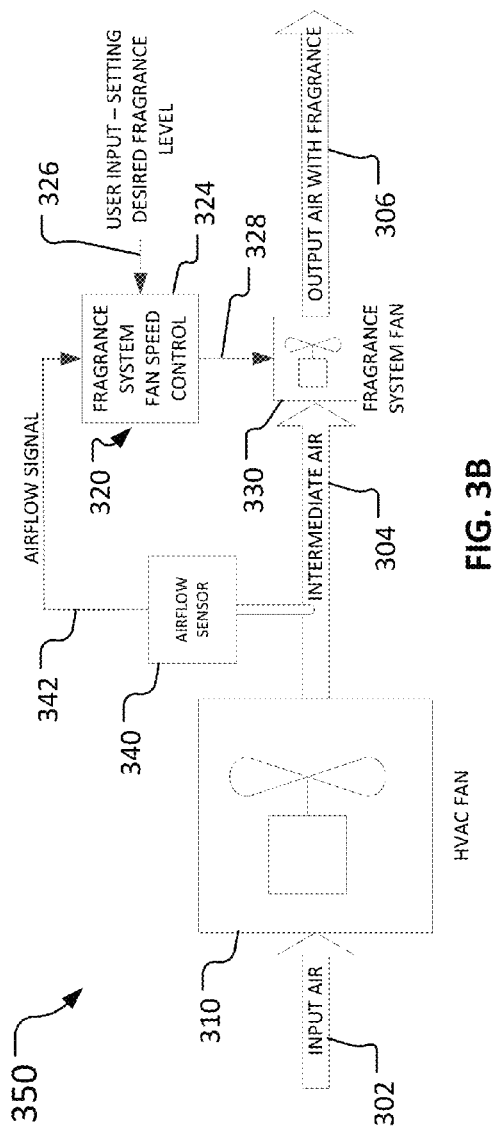

HVAC FRAGRANCE SYSTEM

CROSS-REFERENCE TO RELATED APPLICATIONS

This application claims the benefit of U.S. Provisional Application Ser. No. 61/809,372, filed Jul. 23, 2013. The disclosure of the prior application is considered part of (and is incorporated by reference in) the disclosure of this application.

BACKGROUND

1. Technical Field

This document relates to systems and methods for enhancing heating, ventilation, and air-conditioning (HVAC) systems. For example, this document relates to systems and methods for injecting fragrances into a ventilation airstream of an HVAC system.

2. Background Information

The main purpose of an HVAC system is to maintain good indoor air quality with adequate ventilation and thermal comfort. Proper heating, ventilating, and air-conditioning are important to maintaining a comfortable, healthy, and productive indoor environment. Many types of buildings use HVAC systems, including commercial buildings, restaurants, stores, homes, schools, and hospitals. In addition, vehicles, such as cars, buses, trains, and airplanes, use HVAC systems. HVAC systems usually require the use of fans and ductwork to distribute air throughout the space served by the HVAC system.

SUMMARY

This document provides systems and methods for enhancing HVAC systems. For example, this document provides systems and methods for integrating a fragrance injection system with an HVAC system. The fragrance injection system can add fragrance into the ventilation airstream provided by the HVAC system. In some embodiments, the fragrance injection system includes a fan that forces fragranced air into the HVAC airstream. In some embodiments, the speed of the fragrance system fan is automatically controlled based on an amount of airflow in the HVAC airstream.

In general, one aspect of this document features a system for injecting a fragrance into an airstream of an HVAC unit. The system comprises a structure configured to receive one or more fragrance sources; a fragrance system fan configured to move air past an active fragrance source of the one or more fragrance sources and to move the air into the airstream of the HVAC unit; and a controller module including a user interface for receiving user input. The controller module is configured to (i) receive an airflow input signal that indicates an amount of airflow in the airstream, (ii) determine a fragrance system fan speed signal based on the airflow input signal, (iii) output the fragrance system fan speed signal such that the fragrance system fan speed signal can control a speed of the fragrance system fan, and (iv) periodically adjust the fragrance system fan speed signal in response to a change in the airflow input signal.

In various implementations of the system for injecting a fragrance into an airstream of an HVAC unit, the airflow input signal may comprise a signal indicating a speed of a fan of the HVAC unit. Optionally, the airflow input signal may comprise a signal indicating an air pressure in the airstream, an air velocity in the airstream, or a volumetric airflow amount in the airstream. In some embodiments, the fragrance system may comprise two or more fragrance sources. The structure configured to receive one or more fragrance sources may be an enclosure in some embodiments. The structure may also optionally comprise a rotary actuator. In particular embodiments, the user interface may be configured to receive a user input that causes a rotation of the rotary actuator in response to a condition established by the user input. In some examples, the condition is a time of day. The structure configured to receive one or more fragrance sources may be configured to receive two or more fragrance sources in some embodiments. Optionally, the user interface may be configured to have internet connectivity such that user input can be received by the user interface via the internet. In some embodiments of the system, the system further comprises the HVAC unit, and the HVAC unit may be configured for use in conjunction with a building. In alternative embodiments of the system, the system further comprises the HVAC unit, and wherein the HVAC unit may be configured for use in conjunction with a vehicle.

In another aspect, this document features a method for controlling a speed of a fan of a fragrance system that is configured to inject a fragrance into an airstream of an HVAC unit. The method comprises receiving, by a controller module of the fragrance system, an airflow input signal that indicates an amount of airflow in the airstream; determining, by the controller module of the fragrance system, a fragrance system fan speed signal based on the airflow input signal; and outputting, by the controller module of the fragrance system, the fragrance system fan speed signal such that the fragrance system fan speed signal controls a speed of the fragrance system fan.

In various implementations of the method for controlling a speed of a fan of a fragrance system that is configured to inject a fragrance into an airstream of an HVAC unit, the fragrance system fan speed signal may also be based on a user input that establishes a relationship between the airflow input signal and the fragrance system fan speed signal. In some implementations, the relationship comprises a ratio. The method may further comprise adjusting the fragrance system fan speed signal by repeating the receiving, determining, and outputting steps in some embodiments. Optionally, the adjusting the fragrance system fan speed signal may be performed on a periodic time-based basis.

In another general aspect, this document features a computer-readable storage device storing software comprising instructions executable by one or more computers which, upon such execution, cause the one or more computers to perform operations comprising: receiving, by a controller module of a fragrance system, an airflow input signal that indicates an amount of airflow in an airstream of an HVAC system; determining, by the controller module of the fragrance system, a fragrance system fan speed signal based on the airflow input signal; and outputting, by the controller module of the fragrance system, the fragrance system fan speed signal such that the fragrance system fan speed signal controls a speed of a fragrance system fan.

Particular embodiments of the subject matter described in this document can be implemented to realize one or more of the following advantages. In some embodiments provided herein, the fragrance system is configured to be readily retrofitted to existing HVAC system. In some embodiments, the HVAC fragrance systems provided herein are flexibly programmable to operate as desired by a user. For example, the fragrance system can be programmed for a particular pattern of intermittent administration of a fragrance, administration of different fragrances, administration of different levels of fragrance, and the like. In some embodiments, the speed of the fragrance system fan can automatically modulate in keeping with the amount of airflow in the HVAC airstream. Accordingly, the level of fragrance added to the airstream of the HVAC system can be consistently maintained even when the flow rate of the airstream varies.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 3A is a schematic diagram of a control system of a fragrance system in accordance with some embodiments provided herein.

FIG. 3B is a schematic diagram of another control system of a fragrance system in accordance with some embodiments provided herein.

Like reference numbers represent corresponding parts throughout.

DETAILED DESCRIPTION

In homes, work places, and vehicles, many people enjoy a fragranced environment. Research shows the use of fragrances can result in a number of different positive psychological impacts. For example, pleasant aromas may heighten people's senses and enhance the learning process. In some cases, fresh scents may help keep people mentally alert. Fragrances can also boost positive moods, such as providing a feeling of calmness in the midst of stressful circumstances. In fact, certain fragrances have been shown to reduce stress as measured physiologically by lowered blood pressure, reduced muscle tension, or reduced startle reflex. Fragrance can be an important cue to consumers of cleanliness. There is also evidence that odors may influence human responses to pain. Such findings may be attributable to odors directing attention away from the pain, or to the fact that odors may influence moods that in turn may modify the unpleasantness or intensity of pain. Fragrances can also have a positive effect in the work environment. Recent studies have shown that periodic administration of pleasant fragrances during a task requiring sustained attention improves work performance.

This document provides systems and methods for enhancing HVAC systems. For example, this document provides systems and methods for injecting fragrances into a ventilation airstream of an HVAC system. In some embodiments, the speed of the fragrance system fan is automatically based on the amount of airflow in the HVAC airstream. As such, the fragrance level of an HVAC airstream can be maintained at a consistent intensity despite interruptions or fluctuations in HVAC fan speed.

Figure 1:
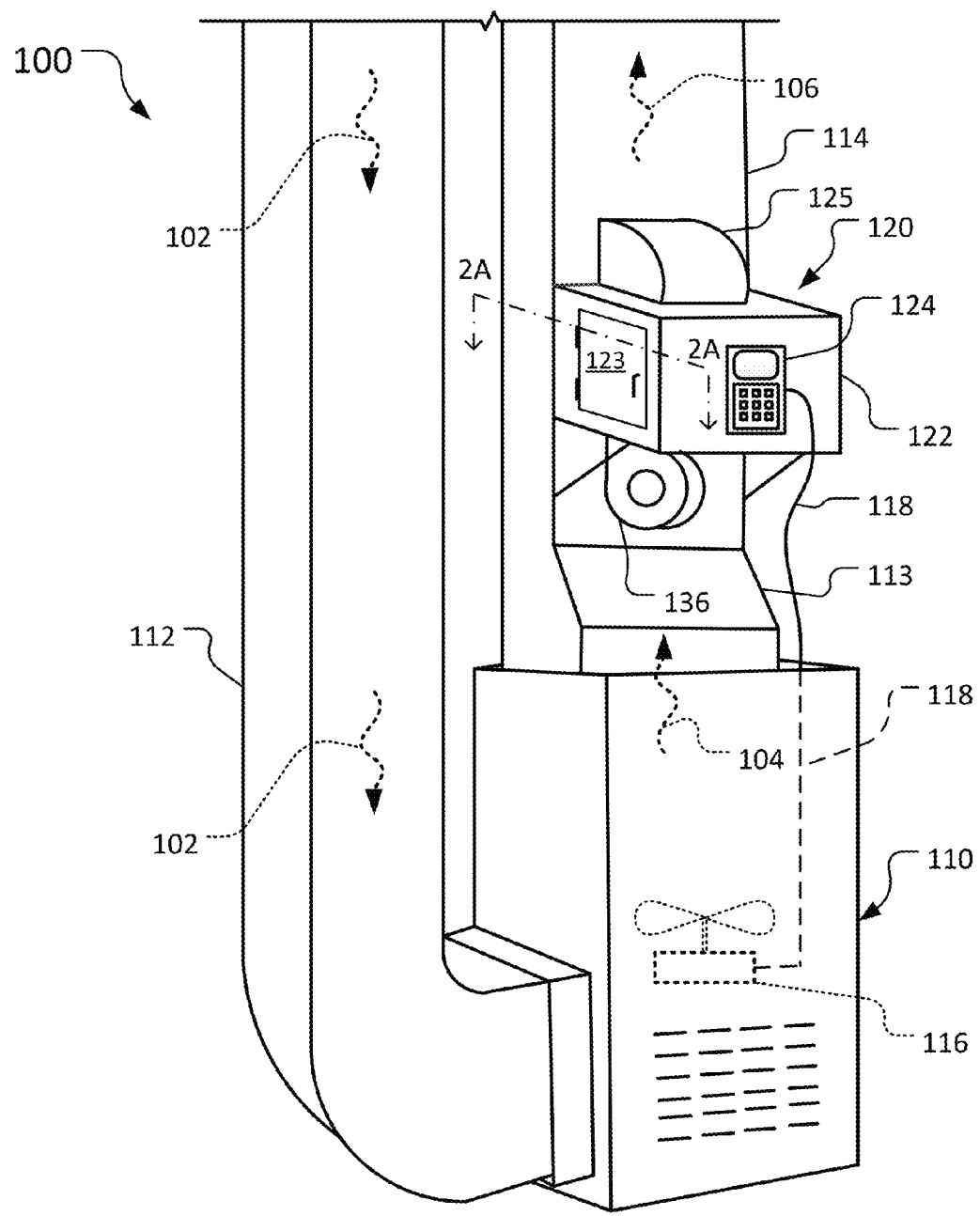
FIG. 1 is perspective view of an HVAC system including a fragrance system in accordance with some embodiments provided herein.

Referring to FIG. 1, an HVAC system 100 in accordance with some embodiments provided herein can include an HVAC unit 110 and a fragrance system 120. The HVAC unit 110 represents a typical HVAC system that is commonly used as a source of ventilation in a home or other type of building. The fragrance system 120 can be included to function in cooperation with HVAC unit 100. The fragrance system 120 can inject a fragrance into the air that is supplied by the HVAC unit 110. Accordingly, the space receiving air from HVAC system 100 can include a fragrance. As will be described further, the type and intensity of the fragrance can be controlled as desired by a user of the HVAC system 100.

In the depicted implementation, the fragrance system 120 is shown installed on a typical home HVAC unit 110. However, it should be understood from the description herein that the fragrance system 120 is scalable. That is, in some embodiments the fragrance system 120 can be made smaller than depicted (even miniaturized). Some such smaller embodiments may be well-suited for use, for example, in conjunction with vehicles (e.g., cars, buses, airplanes, trains, etc.) or for an individual room or zone of a building. The fragrance system 120 can also be made larger than depicted. Accordingly, the fragrance system 120 can be implemented in the context of large HVAC systems and/or multiple HVAC systems that service large buildings.

In the depicted implementation, the fragrance system 120 is installed to inject fragrance into the ventilation airstream as it exits the HVAC unit 110. In alternative embodiments, the fragrance system 120 can be installed to inject fragrance into the ventilation airstream that is returning to the HVAC unit 110.

While in the depicted implementation the fragrance system 120 is located in close proximity to the HVAC unit 110, close proximity is not required in all implementations. In some implementations, the fragrance system 120 can be located farther away from the HVAC unit 110.

In particular embodiments, multiple fragrance systems 120 are included as part of a single HVAC system 100. In some such embodiments, different zones or rooms of the building receiving the airstream from the HVAC system 100 may be independently serviced by a particular fragrance system 120. Accordingly, one particular zone or room can be fragranced independently from another particular zone or room. In one example, one room may receive a particular fragrance and another room of the same building may receive a different fragrance. It should be understood from the description herein that the fragrance systems 120 can be flexibly implemented and operated in a wide variety of configurations and manners.

Still referring to FIG. 1, the HVAC system 100 includes a return duct 112, an intermediate duct 113, and a supply duct 114. The return duct 112 is used to convey a return airstream 102 to the HVAC unit 110. Within the HVAC unit 110, the return airstream 102 may be filtered, cooled, heated, humidified, and/or otherwise conditioned. Intermediate airstream 104 exits the HVAC unit 110. The intermediate duct 113 receives the intermediate airstream 104. The intermediate duct 113 conveys the intermediate airstream 104 towards the fragrance system 120. As will be described further below, the fragrance system 120 may inject fragrance-laden air into the intermediate airstream 104 that thereafter becomes a supply airstream 106 that is conveyed to the space(s) being supplied by the HVAC system 100. In some embodiments, the supply duct 114 divides into multiple branches that supply individual rooms or individual vents within a room, and the like.

The HVAC unit 110 includes an HVAC fan 116. The HVAC fan 116 is used to pressurize the air within the HVAC system 100 so that it flows as desired, such as in the direction described above. The HVAC fan 116 may operate at various speeds, intermittently (on/off), or a combination of both. In some cases, the operation of the HVAC fan 116 is effected by thermostatic controls. In some cases, the operation of the HVAC fan 116 is effected by a building automation system that is programmed to enhance the energy efficiency and occupant comfort provided by HVAC system 100.

A fan speed signal 118 provides an indication of the operational speed of the HVAC fan 116. In some embodiments, the fan speed signal 118 is a variable voltage signal, amperage signal, pulse signal, or a waveform, and the like, that is indicative of the speed of the HVAC fan 116. The speed of the HVAC fan 116 is indicative of the amount of airflow in the intermediate airstream 104.

In some embodiments, the fragrance system 120 has a structure including an enclosure 122, an access panel 123, a controller module 124, and a variable speed fragrance system fan 136. The controller module 124 includes a user interface system for the fragrance system 120. Accordingly, the controller module 124 is equipped to accept user input via, for example, a touchscreen, buttons, switches, and the like. The controller module 124 may also equipped to provide user output via a display, indicator lights, audible tones, and the like.

In some implementations, the controller module 124 is located remotely away from the enclosure 122. For example, in some implementations it may be convenient to locate the controller module 124 in an occupied room, such as near a thermostat that controls the HVAC unit 110. In some implementations, a first controller module 124 is located near the enclosure 122, and one or more additional controller modules 124 are located remotely away from the enclosure 122. In some embodiments, the functions of the controller module 124 may be integrated with other devices such as a thermostat, building automation system, and the like.

In some embodiments, the controller module 124 is programmable. By programming the controller module 124, the operational parameters of the fragrance system 120 can be established by a user and the controller module 124 can automatically control the fragrance system 120 thereafter, in accordance with the parameters established by the user.

The controller module 124 may be programmed to control a wide variety of operational parameters of the fragrance system 120. For example, the controller module 124 can be programmed to automatically adjust the intensity of the fragrance depending on the day of the week, the time of the day, or both. In another example, the controller module 124 can be programmed to adjust the type of fragrance that is actively being injected, because in some embodiments the fragrance system 120 can be loaded with multiple types of different fragrances. For example, the fragrance system 120 may be programmed to inject a first fragrance during the daytime and a different fragrance during the evening.

In some embodiments, the controller module 124 has connectivity to the internet. In such cases, the control module 124 can receive user input remotely so that the fragrance system 120 can be remotely controlled over the internet by the user. In some embodiments, the controller module 124 is configured to operate using a wireless data communication technique, such as Wi-Fi or another wireless communication technique. In some such embodiments, a Wi-Fi router or other like device can wirelessly connect the controller module 124 to the internet. In other embodiments, the internet connection can be a wired connection. In any case, using an internet-connected controller module 124 can allow the user to monitor and adjust the operational parameters of the fragrance system 120 using a computing device such as a smartphone, tablet, or other web-enabled device from anywhere in the world where an internet connection is available.

The controller module 124 receives the fan speed signal 118. The fan speed signal 118 provides an indication of the operational speed of the HVAC fan 116. In some embodiments, the controller module 124 is programmed to control the speed of the fragrance system fan 136 in a consistent ratio to the speed of the HVAC fan 116 as indicated by the fan speed signal 118. In such cases, as the speed of the HVAC fan 116 changes, the controller module 124 automatically changes the speed of the fragrance system fan 136 to maintain a constant speed ratio between the speed of the HVAC fan 116 and the fragrance system fan 136. In this manner, the intensity of the fragrance in the supply airstream 106 can be automatically maintained substantially consistently despite changes in the airflow amount delivered from the HVAC unit 110.

Figure 2A:
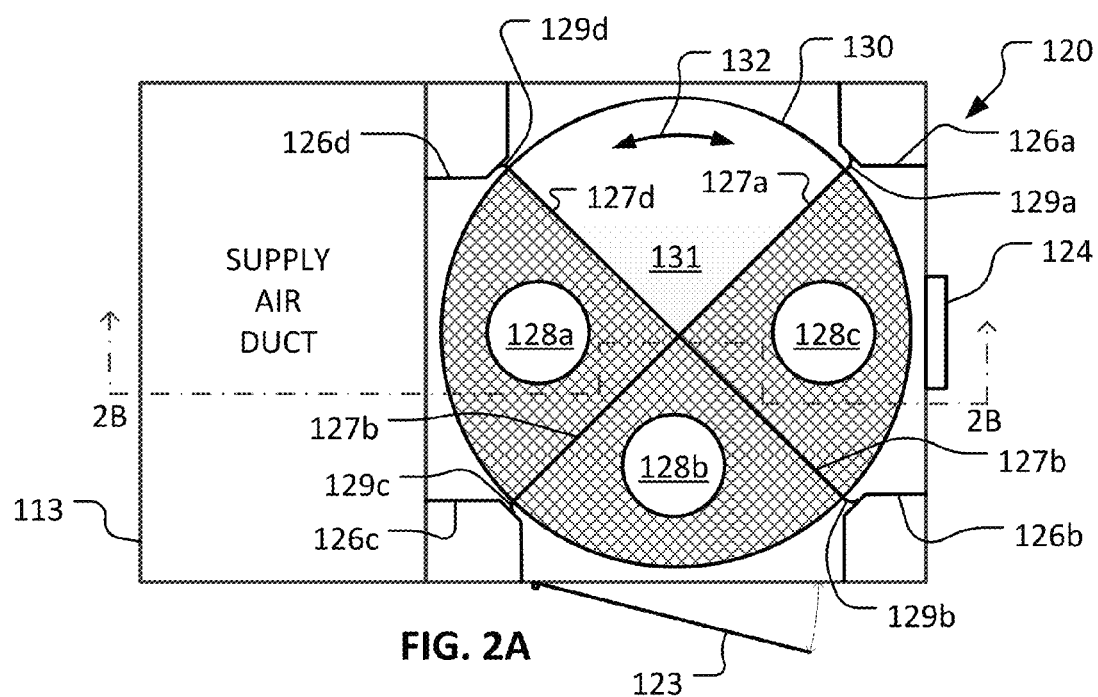
FIG. 2A is a sectional top view of the fragrance system of FIG. 1.
Figure 2B:
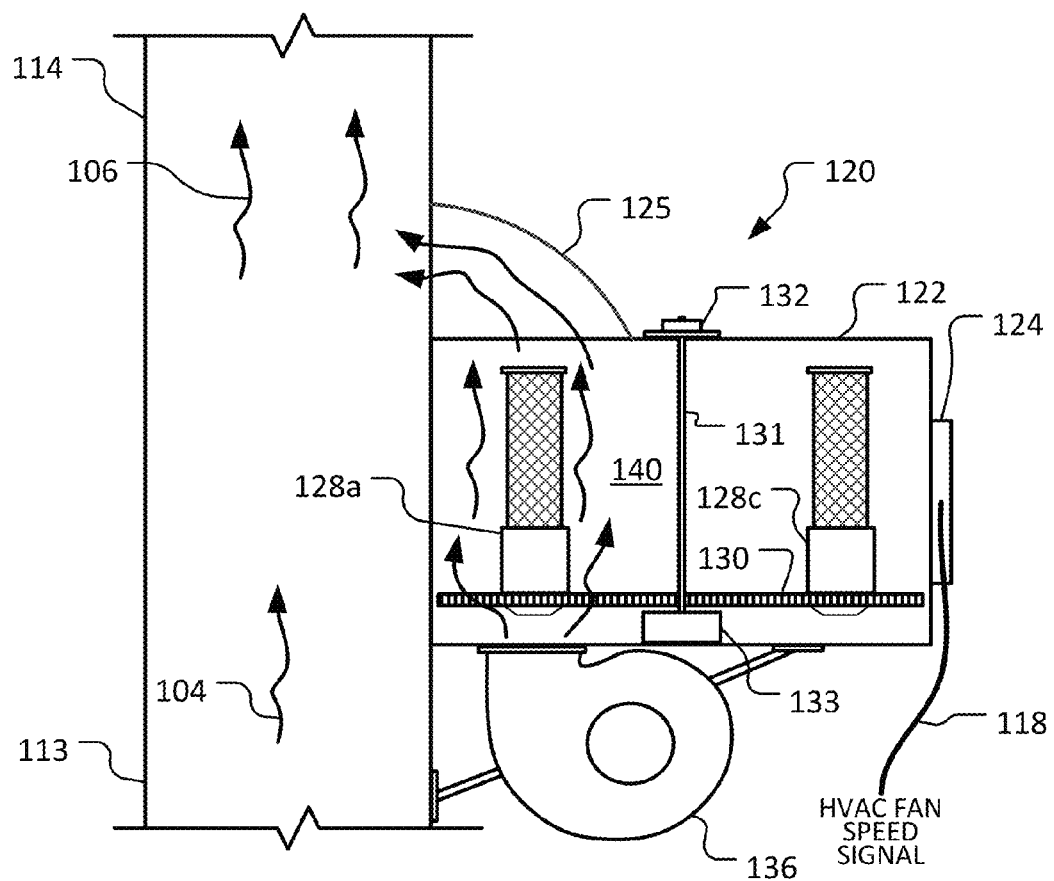
FIG. 2B is a partial sectional side view of the fragrance system of FIG. 1.

Referring now to FIGS. 1, 2A, and 2B, in some embodiments the fragrance system 120 includes multiple fragrance sources 128a, 128b, and 128c that are received in the structural enclosure 122. FIG. 2A is a horizontal cross-sectional view of the fragrance system 120 taken along section line 2A-2A of FIG. 1. FIG. 2B is a partial vertical cross-sectional view of the fragrance system 120 taken along section line 2B-2B of FIG. 2A.

In the depicted embodiment, the fragrance sources 128a, 128b, and 128c are located on a rotary table 130. The fragrance sources 128a, 128b, and 128c are illustrated as including a liquid reservoir and a wick. However, it should be understood that the fragrance sources 128a, 128b, and 128c can be many other types of fragrance sources in other embodiments, such as, but not limited, to gels, solids, aerosol sprays, atomizers, piezoelectric atomizer devices, and the like. The fragrance system 120 is configured to allow the fragrance sources 128a, 128b, and 128c to be removed from the interior or the enclosure 122 and replaced with a different fragrance source as desired by a user of the fragrance system 120. For example, the access panel 123 can be opened to gain access to change out the fragrance sources 128a, 128b, and 128c. In particular, in the depicted orientation, the fragrance canister 128b can be accessed via the access panel 123. To access the other fragrance canisters 128a and 128c, the rotary table 130 can be rotated (by a user input to the controller module 124) to positioned them next to the access panel 123.

In some implementations, the multiple fragrance sources 128a, 128b, and 128c are different fragrances. However, the multiple fragrance sources 128a, 128b, and 128c can alternatively include two or three sources of the same fragrance.

In the depicted embodiment, the interior space of the enclosure 122 is divided into four interior quadrants by divider walls 127a, 127b, 127c, and 127d. The divider walls 127a, 127b, 127c, and 127d are attached at their lower edges to the rotary table 130 and extend upward from the rotary table 130 such that their upper edges are just slightly below the top of the enclosure 122 (where a seal material may be included therebetween). In some embodiments, the divider walls 127a, 127b, 127c, and 127d are constructed of sheet metal such as galvanized sheet metal, stainless steel, aluminum, and the like. In some embodiments, polymeric materials may be used to construct the divider walls 127a, 127b, 127c, and 127d.

In some embodiments, the outer vertical edges of the divider walls 127a, 127b, 127c, and 127d include integral seals 129a, 129b, 129c, and 129d respectively. In some embodiments, the seals 129a, 129b, 129c, and 129d are a flexible gasket material such as foam rubber, silicone, felt, and the like. The seals 129a, 129b, 129c, and 129d extend from the divider walls 127a, 127b, 127c, and 127d and make contact with corner spacers 126a, 126b, 126c, and 126d respectively, when the rotary table 130 is positioned as shown. In the configuration shown, the orientation of the divider walls 127a, 127b, 127c, and 127d, the seals 129a, 129b, 129c, and 129d, and the corner spacers 126a, 126b, 126c, and 126d cooperate to divide the interior of the enclosure 122 into four generally sealed interior quadrants. In other embodiments, the enclosure is divided into fewer than four or more than four interior spaces.

In the depicted embodiment, the fragrance canister 128a is in a first of the four interior quadrants; the fragrance canister 128b is in a second of the four interior quadrants; the fragrance canister 128c is in a third of the four interior quadrants; and blank 131 is in a fourth of the four interior quadrants. As described above, since the four interior quadrants are generally sealed spaces, the fragrance sources 128a, 128b, and 128c are isolated from each other.

The interior quadrant above the fragrance system fan 136 is the active quadrant 140. The active quadrant 140 is the quadrant that is confluent with the ducts 113 and 114 of the HVAC system 100, and the fragrance system fan 136. Accordingly, when a fragrance canister is positioned within the active quadrant 140 and the fragrance system fan 136 is operating, then fragrance-laden air is being injected into the airstream of the HVAC system 100. Meanwhile, the other three quadrants are inactive and are generally sealed off from the active quadrant 140.

The rotary table 130 can be rotated as indicated by arrow 132. The controller module 124 can initiate and control the rotation of the rotary table 130 in accordance with user commands entered into the controller module 124. In one example, the controller module 124 may initiate a 90° clockwise rotation of rotary table 130 to position the fragrance canister 128b in the active quadrant 140. In that fashion, a change to the type of fragrance being injected into the supply airstream 106 can be initiated. In another example, the controller module 124 may initiate a 90° counter-clockwise rotation of rotary table 130 to position the blank 131 in the active quadrant 140. The blank 131 shuts off all injection of fragrance from the fragrance system 120. In another example, the controller module 124 may initiate a 180° clockwise (or counter-clockwise) rotation of rotary table 130 to position the fragrance canister 128c in the active quadrant 140. It should be understood from the description herein, that the controller module 124 can actuate rotations of the rotary table 130 to position any particular fragrance source 128a, 128b, or 128c (or blank 131) in the active quadrant 140 in response to user input that pre-establishes (programs) the operations of the fragrance system 120.

In some embodiments, the user can input to the controller module 124 the type of fragrance that is positioned in each of the quadrants. For example, the user may install a vanilla fragrance canister as the fragrance source 128a, a lilac fragrance canister as the fragrance source 128b, and an evergreen fragrance as the fragrance source 128c. The user can then input into the controller module 124 those types of fragrances and the positions in which they are installed. In some such embodiments, the user can then program the controller module 124, for example, to activate the lilac fragrance from 8:00 am to 11:00 am; the vanilla fragrance from 11:00 am to 2:30 pm; no fragrance from 2:30 pm to 3:45 pm; the evergreen fragrance from 3:45 pm to 6:00 pm; and no fragrance from 6:00 pm to 8:00 am. In other such example, the user can additionally, or alternatively, program a first fragrance to be active on particular days of the week, and a second fragrance on other days of the week, and so on. For example, the user may program one fragrance to be active on Monday through Friday, and a different fragrance on the weekends.

In some embodiments, the user can also program the controller module 124 to deliver a corresponding intensity level for each of the fragrances. Or, the user can program the controller module 124 to adjust the intensity level during a period of delivering a particular fragrance. For example, the user may program the controller module 124 to start out delivering a lesser amount of fragrance at the beginning of a period of delivering a particular fragrance, and an increasing amount after a period of time. The controller module 124 can adjust the intensity of the fragrance by adjusting the speed of the fragrance system fan 136 in relation to the amount of airflow in the intermediate airstream 104.

Referring to FIG. 2B in particular, the fragrance system fan 136 blows air into the active quadrant 140, past the fragrance canister 128a, into a transition duct 125, and into the supply duct 114. At least portions of the rotary table 130 are porous to allow airflow therethrough as shown. For example, in some embodiments portions of the rotary table 130 are made of expanded metal such as galvanized steel, stainless steel, aluminum expanded metal, and the like. The blank 131, however, can be a solid portion of sheet metal in some embodiments. Accordingly, when the blank 131 is positioned in the active quadrant 140, no fragrance will be injected into the supply airstream 106 because the fragrance sources 128a-b-c will be essentially sealed off from the ducts 113 and 114.

A vertical shaft 131 is at the center of the rotary table 130. The inner edges of the divider walls 127a, 127b, 127c, and 127d can be attached to the vertical shaft 131. The top of the vertical shaft 131 is coupled with a bearing 132. The bearing 132 can be, for example, a ball bearing, needle bearing, roller bearing, polymeric bushing, metallic bushing, and the like. The bottom of the vertical shaft 131 is coupled with a rotary actuator 133. The rotary actuator 133 provides the driving force to rotate the rotary table 130. In some embodiments, the rotary actuator 133 is a motor. For example, the rotary actuator 133 can be a DC motor, AC motor, stepper motor, servomotor, and the like. A gear reduction system or belt drive system may be included as part of the rotary actuator 133 in some embodiments. In some embodiments, the rotary actuator 133 can be a fluid-powered device such as a rotary pneumatic actuator or rotary hydraulic actuator. In other embodiments, other types of rotary actuators can be used for rotary actuator 133. In any case, activation of the rotary actuator 133 motions are initiated from the controller module 124 such that the controller module 124 determines whether fragrance canister 128a, 128b, 128c, or blank 133 is positioned in the active quadrant 140.

The controller module 124 also controls operations of the fragrance fan 136. That is, the controller module 124 controls the speed of the variable speed fragrance fan 136, and whether the fragrance fan 136 is on or off. In some embodiments, an additional fan motor drive system is included and the controller module 124 controls the fragrance fan 136 through the motor drive system that is connected to the fragrance fan 136. In general, when the controller module 124 increases the speed of the fragrance fan 136, a greater intensity of fragrance is injected into the supply airstream 106. Conversely, when the controller module 124 decreases the speed of the fragrance fan 136, a lesser intensity of fragrance is injected into the supply airstream 106. Accordingly, the controller module 124 can adjust the intensity of the fragrance injected into the supply airstream 106.

As described previously, the HVAC fan speed signal 118 is electrically connected to the controller module 124 in some embodiments. As such, in some cases the controller module 124 may be programmed to control the speed of the fragrance fan 136 in correspondence to the HVAC fan speed signal 118. For example, in some implementations the controller module 124 may be programmed to control the fragrance fan 136 in a consistent ratio with the HVAC fan speed signal 118. Accordingly, as the HVAC fan 116 slows down, the fragrance fan 136 will also slow down to maintain a consistent speed ratio and a substantially consistent intensity of the fragrance in the supply airstream 106. Conversely, as the HVAC fan 116 speeds up, the fragrance fan 136 will also speed up to maintain a consistent speed ratio and a substantially consistent intensity of the fragrance in the supply airstream 106.

In some embodiments, the controller module 124 can be programmed to utilize various other more complex speed control algorithms rather than a simple consistent ratio between the HVAC fan speed signal 118 and the fragrance fan 136. In some such embodiments, the HVAC fan speed signal 118 is used as an input to the algorithm run by the controller module 124, and the output of the algorithm determines the speed of the fragrance fan 136. Other inputs to the algorithm may also be included, such as, but not limited to, the type of fragrance, the point in time during the delivery of a particular fragrance cycle (e.g., the beginning, middle, or end of a cycle), the time of day, the day of the week, the season of the year, and the like.

FIG. 3A provides a schematic diagram of an HVAC system 300 that includes a fragrance system 320 in accordance with some embodiments. Input air 302 enters the HVAC fan 310. Intermediate air 304 exits the HVAC fan 310 and approaches the fragrance system fan 330. Output air with fragrance 306 exits the area of the fragrance system 330.

An HVAC fan speed signal 318 is electrically connected between the HVAC fan 310 (or drive system thereof) and a fragrance system fan speed control 324. In some embodiments, the fragrance system fan speed control 324 can be a controller module (such as the controller module 124 as described above). A user input 326 is received by the fragrance system fan speed control 324. For example, the user input 326 can be one or more inputs to program the fragrance system fan speed control 324. The fragrance system fan speed control 324 outputs a fragrance system fan speed signal 328 to the fragrance system fan 330 (or a drive system thereof). The fragrance system fan speed signal 328 may be based on the HVAC fan speed signal 318 and the user input 326 in some implementations. For example, as described above, in some implementations the fragrance system fan speed control 324 may be programmed to maintain the speed of the fragrance system fan 330 in a consistent ratio to the speed of the HVAC fan 310. In other implementations, other algorithms may be used for controlling the speed of the fragrance system fan 330. Such algorithms may or may not be based on the HVAC fan speed signal 318 received at the fragrance system fan speed control 324.

FIG. 3B provides a schematic diagram of another HVAC system 350 that includes a fragrance system 320 in accordance with some embodiments. Input air 302 enters the HVAC fan 310. Intermediate air 304 exits the HVAC fan 310 and approaches the fragrance system fan 330. Output air with fragrance 306 exits the area of the fragrance system 330.

The HVAC system 350 also includes an airflow sensor 340. The airflow sensor 340 is indicative of the amount of airflow in the airstream of the intermediate air 304. An airflow signal 342 is electrically connected between the airflow sensor 340 and the fragrance system fan speed control 324. Accordingly, the fragrance system fan speed control 324 receives a signal that indicates the amount of airflow being delivered by the HVAC fan 310.

The fragrance system fan speed control 324 outputs a fragrance system fan speed signal 328 to the fragrance system fan 330 (or a drive system thereof). The fragrance system fan speed signal 328 may be based on the airflow signal 342 and the user input 326 in some implementations. For example, in some implementations the fragrance system fan speed control 324 may be programmed to maintain the speed of the fragrance system fan 330 in a consistent ratio to the airflow signal 342. In other implementations, other algorithms may be used for controlling the speed of the fragrance system fan 330. Such algorithms may or may not be based on the airflow signal 342 received at the fragrance system fan speed control 324.

Figure 4:
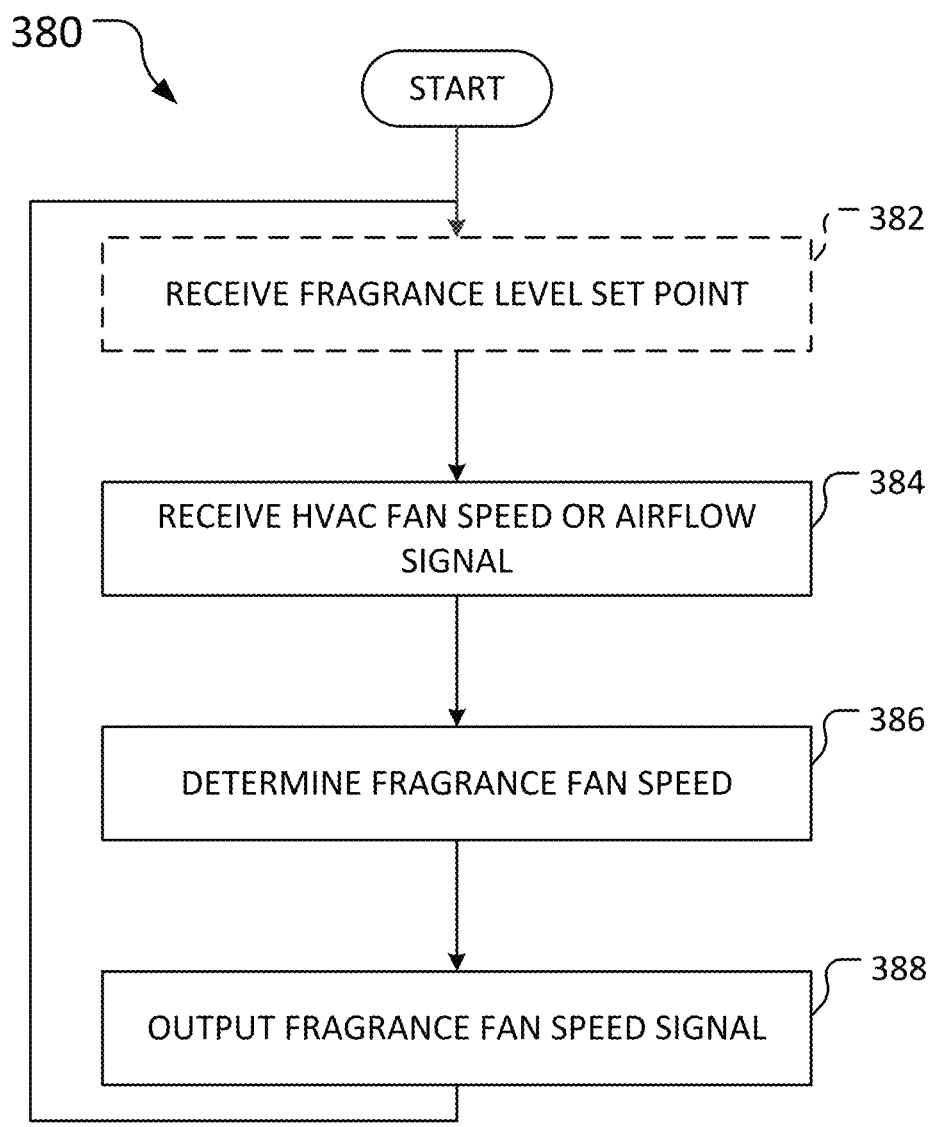
FIG. 4 is flowchart of a method of controlling a fan of a fragrance system in accordance with some embodiments provided herein.
Figure 5:
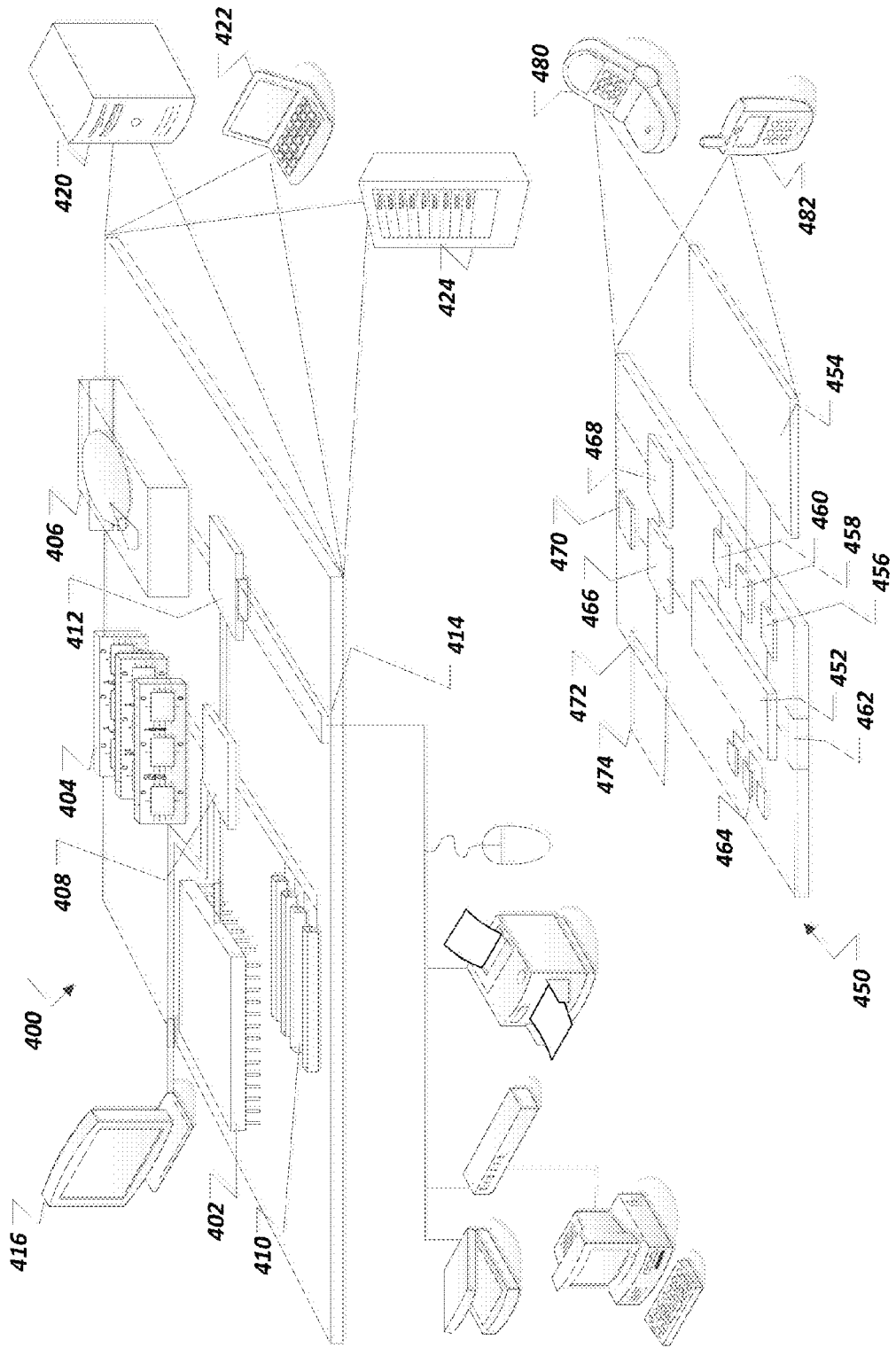
FIG. 5 shows an example system that can be used to implement the systems and techniques described herein.

FIG. 4 illustrates a method 380 for controlling the fan speed of a fragrance injection system. The method 380 may be used in conjunction with the HVAC system 100 for example.

At step 382, a fragrance system fan speed controller optionally receives a fragrance level set point. The set point may be input by a user of the fragrance injection system into a user interface associated with the fragrance system fan speed controller. The fragrance level set point may be characterized in a number of different formats. In one example, the fragrance level set point may be a number on a scale of 1 to 10. In another example, the fragrance level set point may be a low-medium-high type of setting. In another example, the input can be provided by sliding an indicator to a location along a scale. Still other input formats are also envisioned within the scope of this disclosure.

At step 384, the fragrance system fan speed controller receives an HVAC fan speed or airflow signal. The receipt of the HVAC fan speed or airflow signal can be as described above in reference to HVAC fan speed signal 318 of HVAC system 300 or airflow signal 342 of HVAC system 350. These signals give an indication of the amount of airflow arriving at the fragrance system.

At step 386, the fragrance system fan speed controller determines a fragrance system fan speed. The fragrance fan speed may be determined based on the fragrance level set point, or the HVAC fan speed or airflow signal, or both. In one example, the fragrance system fan speed controller may be programmed to maintain a consistent ratio between the amount of airflow arriving at the fragrance system and the fragrance system fan speed. In such a case, when the airflow arriving at the fragrance system (as indicated by the HVAC fan speed or airflow signal) is reduced by 30%, for example, the fragrance system fan speed controller will determine that the fragrance system fan speed should also be reduced by 30%. In this manner, the intensity of the fragrance in the air supplied by the HVAC system will be substantially constant despite variations in the speed of the HVAC fan or airflow arriving at the fragrance system. In other example, other algorithms for determining the fragrance fan speed may be used. Such algorithms may use the fragrance level set point, or the HVAC fan speed or airflow signal, or both, and other inputs as well.

At step 388, the fragrance system fan speed controller provides an output signal to the fragrance system fan (or to a drive control system thereof). The output is based on the determined fragrance fan speed from step 430. The output signal to the fragrance system fan can control the speed of the fragrance system fan.

The method 380 can be repeated periodically, such as about every second, about every 5 seconds, about every 10 seconds, or any other suitable time period. Such periodic time periods may be user-selectable in some embodiments.

FIG. 4 shows an example of a computing device 400 and an example of a mobile computing device that can be used to implement the techniques described here. The computing device 400 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 400 includes a processor 402, a memory 404, a storage device 406, a high-speed interface 408 connecting to the memory 404 and multiple high-speed expansion ports 410, and a low-speed interface 412 connecting to a low-speed expansion port 414 and the storage device 406. Each of the processor 402, the memory 404, the storage device 406, the high-speed interface 408, the high-speed expansion ports 410, and the low-speed interface 412, are interconnected using various busses, and may be mounted on a common motherboard or in other manners as appropriate. The processor 402 can process instructions for execution within the computing device 400, including instructions stored in the memory 404 or on the storage device 406 to display graphical information for a GUI on an external input/output device, such as a display 416 coupled to the high-speed interface 408. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 404 stores information within the computing device 400. In some implementations, the memory 404 is a volatile memory unit or units. In some implementations, the memory 404 is a non-volatile memory unit or units. The memory 404 may also be another form of computer-readable medium, such as a magnetic or optical disk.

The storage device 406 is capable of providing mass storage for the computing device 400. In some implementations, the storage device 406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The computer program product can also be tangibly embodied in a computer- or machine-readable medium, such as the memory 404, the storage device 406, or memory on the processor 402.

The high-speed interface 408 manages bandwidth-intensive operations for the computing device 400, while the low-speed interface 412 manages lower bandwidth-intensive operations. Such allocation of functions is exemplary only. In some implementations, the high-speed interface 408 is coupled to the memory 404, the display 416 (e.g., through a graphics processor or accelerator), and to the high-speed expansion ports 410, which may accept various expansion cards (not shown). In the implementation, the low-speed interface 412 is coupled to the storage device 406 and the low-speed expansion port 414. The low-speed expansion port 414, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 420, or multiple times in a group of such servers. In addition, it may be implemented in a personal computer such as a laptop computer 422. It may also be implemented as part of a rack server system 424. Alternatively, components from the computing device 400 may be combined with other components in a mobile device (not shown), such as a mobile computing device 450. Each of such devices may contain one or more of the computing device 400 and the mobile computing device 450, and an entire system may be made up of multiple computing devices communicating with each other.

The mobile computing device 450 includes a processor 452, a memory 464, an input/output device such as a display 454, a communication interface 466, and a transceiver 468, among other components. The mobile computing device 450 may also be provided with a storage device, such as a microdrive or other device, to provide additional storage. Each of the processor 452, the memory 464, the display 454, the communication interface 466, and the transceiver 468, are interconnected using various buses, and several of the components may be mounted on a common motherboard or in other manners as appropriate.

The processor 452 can execute instructions within the mobile computing device 450, including instructions stored in the memory 464. The processor 452 may be implemented as a chipset of chips that include separate and multiple analog and digital processors. The processor 452 may provide, for example, for coordination of the other components of the mobile computing device 450, such as control of user interfaces, applications run by the mobile computing device 450, and wireless communication by the mobile computing device 450.

The processor 452 may communicate with a user through a control interface 458 and a display interface 456 coupled to the display 454. The display 454 may be, for example, a TFT (Thin-Film-Transistor Liquid Crystal Display) display or an OLED (Organic Light Emitting Diode) display, or other appropriate display technology. The display interface 456 may comprise appropriate circuitry for driving the display 454 to present graphical and other information to a user. The control interface 458 may receive commands from a user and convert them for submission to the processor 452. In addition, an external interface 462 may provide communication with the processor 452, so as to enable near area communication of the mobile computing device 450 with other devices. The external interface 462 may provide, for example, for wired communication in some implementations, or for wireless communication in other implementations, and multiple interfaces may also be used.

The memory 464 stores information within the mobile computing device 450. The memory 464 can be implemented as one or more of a computer-readable medium or media, a volatile memory unit or units, or a non-volatile memory unit or units. An expansion memory 474 may also be provided and connected to the mobile computing device 450 through an expansion interface 472, which may include, for example, a SIMM (Single In Line Memory Module) card interface. The expansion memory 474 may provide extra storage space for the mobile computing device 450, or may also store applications or other information for the mobile computing device 450. Specifically, the expansion memory 474 may include instructions to carry out or supplement the processes described above, and may include secure information also. Thus, for example, the expansion memory 474 may be provide as a security module for the mobile computing device 450, and may be programmed with instructions that permit secure use of the mobile computing device 450. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 464, the expansion memory 474, or memory on the processor 452. In some implementations, the computer program product can be received in a propagated signal, for example, over the transceiver 468 or the external interface 462.

The mobile computing device 450 may communicate wirelessly through the communication interface 466, which may include digital signal processing circuitry where necessary. The communication interface 466 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 468 using a radio-frequency. In addition, short-range communication may occur, such as using a Bluetooth, WiFi, or other such transceiver (not shown). In addition, a GPS (Global Positioning System) receiver module 470 may provide additional navigation- and location-related wireless data to the mobile computing device 450, which may be used as appropriate by applications running on the mobile computing device 450.

The mobile computing device 450 may also communicate audibly using an audio codec 460, which may receive spoken information from a user and convert it to usable digital information. The audio codec 460 may likewise generate audible sound for a user, such as through a speaker, e.g., in a handset of the mobile computing device 450. Such sound may include sound from voice telephone calls, may include recorded sound (e.g., voice messages, music files, etc.) and may also include sound generated by applications operating on the mobile computing device 450.

The mobile computing device 450 may be implemented in a number of different forms, as shown in the figure. For example, it may be implemented as a cellular telephone 480. It may also be implemented as part of a smart-phone 482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Embodiments and all of the functional operations described in this specification may be implemented in digital electronic circuitry, or in computer software, firmware, or hardware, including the structures disclosed in this specification and their structural equivalents, or in combinations of one or more of them. Embodiments may be implemented as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any form of programming language, including compiled or interpreted languages, and it may be deployed in any form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A system for injecting a fragrance into an airstream of an HVAC unit, the system comprising:
    a structure configured to receive one or more fragrance sources;
    a fragrance system fan coupled to the structure and configured for attachment to ductwork of the HVAC unit such that the fragrance system fan is outside of the airstream of the HVAC unit, the fragrance system fan configured to move air past an active fragrance source of the one or more fragrance sources and then into the airstream of the HVAC unit; and
    a controller module including a user interface for receiving user input including a desired fragrance intensity level, the controller module configured to (i) receive an airflow input signal that indicates an amount of airflow in the airstream of the HVAC unit, (ii) determine a fragrance system fan speed signal in ratio to the airflow input signal and based on the desired fragrance intensity level, (iii) output the determined fragrance system fan speed signal to control a speed of the fragrance system fan, and (iv) periodically automatically adjust the fragrance system fan speed signal in response to a change of the airflow input signal or a change of the desired fragrance intensity level.

2. The system of claim 1, wherein the airflow input signal comprises a signal indicating a speed of a fan of the HVAC unit.

3. The system of claim 1, wherein the airflow input signal comprises a signal indicating an air pressure in the airstream, an air velocity in the airstream, or a volumetric airflow amount in the airstream.

4. The system of claim 1, wherein the system comprises two or more fragrance sources configured to be received by the structure.

5. The system of claim 1, wherein the structure defines an enclosure for receiving the one or more fragrance sources, and the fragrance system fan is coupled to the structure outside of the enclosure.

6. The system of claim 1, wherein the structure comprises a rotary actuator.

7. The system of claim 6, wherein the user interface is configured to receive a user input that causes a rotation of the rotary actuator in response to a condition established by the user input.

8. The system of claim 7, wherein the condition is a time of day.

9. The system of claim 1, wherein the structure is configured to receive two or more fragrance sources.

10. The system of claim 1, wherein the user interface is configured to have internet connectivity such that user input can be received by the user interface via the internet.

11. The system of claim 1, further comprising the HVAC unit, and wherein the HVAC unit is configured for use in conjunction with a building.

12. The system of claim 1, further comprising the HVAC unit, and wherein the HVAC unit is configured for use in conjunction with a vehicle.

13. The system of claim 1, wherein the controller module further comprises a communication channel for receiving the airflow input signal from a controller that controls a speed of a fan of the HVAC unit.

14. The system of claim 1, wherein the structure defines two or more compartments that are individually sealed such that the two or more compartments are physically isolated from each other, and wherein each compartment of the two or more compartments is configured to receive a respective fragrance source of the one or more fragrance sources.

15. The system of claim 14, wherein the system is configured such that the fragrance system fan is in fluid communication exclusively with a first compartment of the two or more compartments.

16. The system of claim 15, wherein the structure comprises a rotary actuator, and wherein an actuation of the rotary actuator puts the fragrance system fan in fluid communication exclusively with a second compartment of the two or more compartments rather than the first compartment.

\* \* \* \* \*